United States Patent [19]
Pedersen et al.

[11] Patent Number: 6,037,172
[45] Date of Patent: Mar. 14, 2000

[54] RETROVIRAL VECTOR, A REPLICATION SYSTEM FOR SAID VECTOR AND AVIAN OR MAMMALIAN CELLS TRANSFECTED WITH SAID VECTOR

[76] Inventors: Finn Skou Pedersen, Praestenhaven 47, DK 8210, Aarhus V; Anders Henrik Lund, Rosenkrantzgade 1, DK 8000, Aarhus C; Jette Lovmand, Tulstrupvej 5, Tulstrup, DK 8240, Hørning; Poul Jørgensen, Klintevej 11, DK 8240; Mogens Duch, Elmevej 4, DK 8240, both of Risskov, all of Denmark

[21] Appl. No.: 09/169,078

[22] Filed: Oct. 9, 1998

Related U.S. Application Data

[63] Continuation of application No. 08/525,849, Sep. 8, 1995, Pat. No. 5,866,411.

[51] Int. Cl.$^7$ .......................... C07H 21/04; C12N 15/11; C12N 15/63
[52] U.S. Cl. ...................... 435/320.1; 435/69.1; 435/440; 435/455; 435/325; 435/349; 536/23.1; 536/24.33
[58] Field of Search .................................. 435/69.1, 440, 435/455, 320.1, 325, 349; 536/24.33, 23.1

[56] References Cited

PUBLICATIONS

Wakefield et al "Minimal Sequence Requirements of a Functional Human Immunodeficiency Virus Type 1 Primer Binding Sequence" *J.of Virology* vol. 68(3):1605–1614, 1994.

Atze et al "Reduced Replications of Human Immunodeficiency Virus Type 1 Mutants that use Reverse Transcriptase Primers other than the Natural tRNA$^{LYS\ 3}$" *J. of Virology* vol. 69(5): 3090–3097, 1995.

Weiss et al "Synthetic Human tRNA$^{LYS\ 3}$ uhe and Natural Bovine tRNA$^{LYS\ 3}$ yU Interact with HIV–1 Reverse Transcriptase and Serve as Primers for Retroviral cDNA Synthesis" *Gene* vol. 111:83–197, 1992.

Lund et al "Murato Primer Binder Sites Interacting with Different tRNAS Allow Efficient Murine Leukemia Virus Replication" *J of Virology* vol. 67(12): 7125–7130, 1993.

Krieg et al "The Use of Synthetic tRNA Gene as a novel Approach to study in vivo Transcription and Chem. in Structure in Yeast" NAR vol. 19(14):3849–3855,1991.

Barat et al "Interaction of HIV–1 Reverse Transcriptase with a Synthetic Form of its Replication Primers, tRNA$^{Lys\ 3}$" NAR vol 19(4): 751–757, 1991.

Barat, C., V. Lullien, O. Schatz, G. Keith, M.T. Nugeyre, F. Gruninger–Leitch, F. Barre–Sinoussi, S.F.J. LeGrice and J.L. Darlix; HIV–1 Reverse Transcriptase Specifically Interacts with the Anticodon Domain of its Cognate Primer t–RNA; The EMBO Journal vol.8, No. 11, pp. 3279–3285 (1989).

Pedersen, F.S. et al., "Control Points for Retroviral Vector Safety: A Look at t MLV Replication Cycle", abstract of paper presented at Goslar, Germany, conferenc Sep. 18, 1994.

Lund et al., Journal of Virology, Feb. 1997, vol. 71, pp. 1191–1195.

Sang–Moo Kang et al., Journal of Virology, Jan. 1997, vol. 71, No. 1, pp. 207–217.

Isel et al., Journal of Biological Chemistry, Dec. 1993, vol. 288,, No. 34, pp. 25269–25272.

Wakefield, et al., Journal of Virology, Oct. 1995, vol. 69, No. 10, pp. 6021–6029.

Isel et al., J. Mol. Biol. (1995) 247, pp. 236–250.

*Primary Examiner*—George C. Elliott
*Assistant Examiner*—Sean McGarry
*Attorney, Agent, or Firm*—The Firm of Gordon W. Hueschen

[57] ABSTRACT

A retroviral vector comprising a retrovirus with infectivity for birds and/or mammals in which at least part of the genomic RNA sequences carrying information for the production of viral proteins required in trans for retroviral replication have been replaced by one or more sequences carrying information to be introduced in a target cell chromosome, characterized in that the primer binding site (PBS) has been modified to a sequence that does not allow strong base pairing with the 3' end or other priming sequence in any naturally occurring tRNA.

9 Claims, 13 Drawing Sheets

FIG. 6
SIMPLE RETROVIRUS:
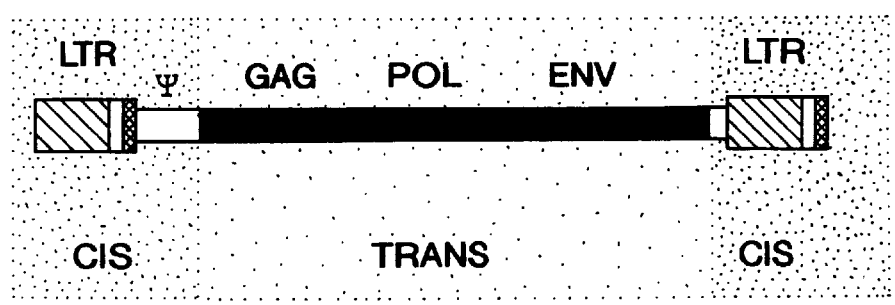
RETROVIRAL VECTOR:

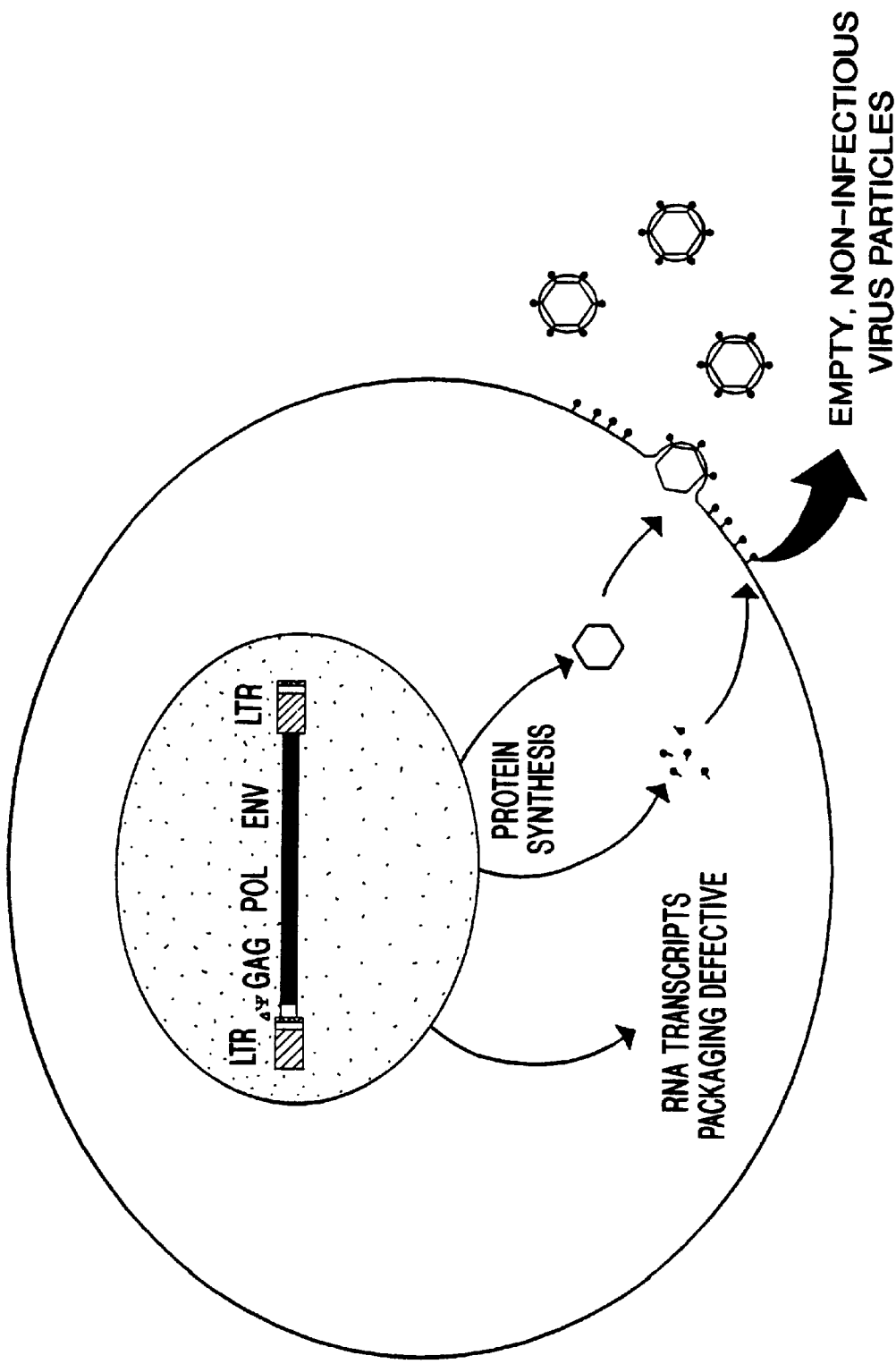

FIG. 8
SIMPLE :
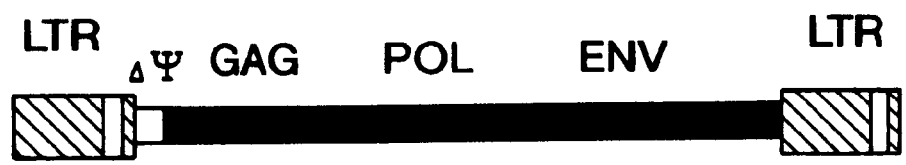
ADVANCED :
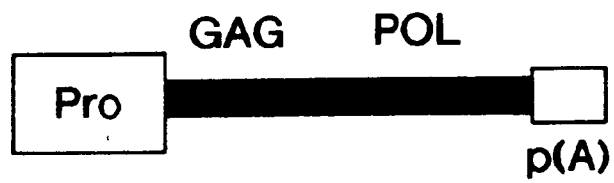
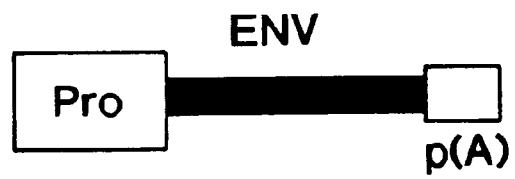

```
                    SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: RNA (genomic)

(iii) HYPOTHETICAL: NO (iv) ANTI-SENSE: NO (vi) ORIGINAL SOURCE:
          (A) ORGANISM: AKV murine leukemia virus (ix) FEATURE:
          (A) NAME/KEY: misc_feature
          (B) LOCATION: 1..18

(xi) SEQUENCE DESCRIPTION: SEQ ID NO:1:
```

-continued

UGGGAUGAAU CUAGGGAU                                                    18

(2) INFORMATION FOR SEQ ID NO:2:

(i) SEQUENCE CHARACTERISTICS:
        (A) LENGTH: 127 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Mus musculus (xi) SEQUENCE DESCRIPTION: SEQ ID NO:2:

CCGGAATTCG AAAACGAAGA AACAAAGTTT ACATCTATGA ATCTGGTCTA GGGGTATGAT      60

TCTCGCTTAG GGTGCGAGAG GTCTAGGGTT CAAATCCCTA GATTCATCAA GTTTTTATAA    120

GCTTTCC                                                              127

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:3:

UCCCCGGCAU CUCCACCA                                                    18

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:4:

CUCCUGGCUG GCUCGCCA                                                    18

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:5:

UUCCCCGACG GGGAGCCA                                                    18

(2) INFORMATION FOR SEQ ID NO:6:

(i) SEQUENCE CHARACTERISTICS:
        (A) LENGTH: 18 base pairs (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:6:

AUCCAGGUGC CCCCUCCA                                                     18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:7:

AUCUCGGUGG GACCUCCA                                                     18

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:8:

AUCUCGGUGG AACCUCCA                                                     18

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:9:

UUCCCGGUCA GGGAACCA                                                     18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:10:

UUCUCGGUCA GGGAACCA                                                     18

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear

```
        (ii) MOLECULE TYPE: tRNA (xi) SEQUENCE DESCRIPTION: SEQ ID NO:11:

UUCCCGGCCA ACGCACCA                                                 18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:12:

AUCCGAGUCA CGGCACCA                                                 18

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:13:

UCCCCGUACG GGCCACCA                                                 18

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:14:

GUCCCUGUUC AGGCGCCA                                                 18

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:15:

GCCCCACGUU GGGCGCCA                                                 18

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:16:
```

```
AACCAUCCUC UGCUACCA                                                     18

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:17:

ACCUCAGAGG GGGCACCA                                                     18

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:18:

UCCUCACACG GGGCACCA                                                     18

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:19:

UCCCGGGUUU CGGCACCA                                                     18

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:20:

AUCCCGGACG AGCCCCCA                                                     18

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:21:

UCCACCUUUC GGGCGCCA                                                     18

(2) INFORMATION FOR SEQ ID NO:22:
```

-continued

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:22:

AUCACGUCGG GGUCACCA                                                 18

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:23:

AACCGGGCGG AAACACCA                                                 18

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: tRNA (xi) SEQUENCE DESCRIPTION: SEQ ID NO:24:

AUCCCUAGAU UCAUCCCA                                                 18

(2) INFORMATION FOR SEQ ID NO:25:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Mus musculus (xi) SEQUENCE DESCRIPTION: SEQ ID NO:25:

GTAGTTCAAA AATATTCGAA AGG                                           23
```

RETROVIRAL VECTOR, A REPLICATION SYSTEM FOR SAID VECTOR AND AVIAN OR MAMMALIAN CELLS TRANSFECTED WITH SAID VECTOR

The present application is a continuation of our prior-filed application Ser. No. 08/525,849, filed Sep. 8, 1995, now U.S. Pat. No. 5,866,411.

This invention concerns a retroviral vector comprising a retrovirus with infectivity for birds and mammals, in which at least part of the genomic RNA sequences carrying information for the production of viral proteins required in trans for retroviral replication have been replaced by one or more sequences carrying information to be introduced in a target cell chromosome. The invention also concerns a tRNA-like primer for reverse transcription of said retroviral vector, a DNA sequence comprising the structural gene sequence of the tRNA-like primer, and a packaging cell line for viral replication of said retroviral vector. Further, the invention concerns an avian or mammalian cell which has been transfected with said retroviral vector.

BACKGROUND OF THE INVENTION

Retroviral vectors are gene transfer vehicles for birds and mammals that exploit features of the retrovirus replication cycle such as high infection efficiency and stable co-linear integration of the virally transmitted information in a target cell chromosome. Retroviral vectors are becoming important tools in basic research, biotechnology and gene therapy.

Most retroviral vectors currently in use are derived from Murine Leukemia Viruses (MLVs). MLVs are particularly suitable as vectors due to their well-documented pattern of transcription in diverse cell types and relatively simple modular genetic structure.

1. Retroviral structure

Retroviruses belong among the enveloped viruses (FIG. 1). The bilipid envelope is derived from the host cell membrane and modified by the insertion of the viral surface protein (SU) and transmembrane protein (TM). The matrix protein (MA) is situated just under the outer membrane surrounding the inner core. The core consists of capsid protein (CA). Inside the capsid are two copies of the retroviral genome which are attached to each other at the 5' end via hydrogen bonding. The virus core particle also contains the viral enzymes: reverse transcriptase (RT), protease (PR), and integrase (IN), and the nucleocapsid protein (NC) which is bound to the viral genome. Besides these proteins encoded by the virus, the virion also contains a number of tRNA molecules derived from the host cell tRNA population.

Murine leukemia viruses (MLV) belong to the simple retroviruses. Retroviruses have a characteristic genomic map: Two long terminal repeats (LTRs) flanking the three structural genes gag, pol and env (FIG. 2). The LTRs can be subdivided into three regions: The U3 region containing enhancer and promoter elements recognized by the cellular transcription machinery, the R region which play an important role during reverse transcription and furthermore contains the polyadenylation signal, and the U5 region containing sequences of importance in reverse transcription and packaging of the retroviral genome. Additionally, the LTRs contain cis elements, the inverted repeats, important during the process of integration (FIG. 3).

The integrated provirus gives rise to two mRNA transcripts, a full-length mRNA encoding the gag-, and the gag-pol polyproteins, and a spliced mRNA encoding the envelope glycoproteins. The full-length mRNA also serves as the genomic RNA and, besides the already described components of the LTR moieties, contains three important cis elements in the 5' untranslated sequence. The primer binding site (PBS), situated downstream from the U5 region, consists of 18 nucleotides complementary to the 3' end of the primer tRNA molecule. Also located in the 5' untranslated region, between the PBS and the beginning of the gag open reading frame, is the packaging signal ($\Psi$). The 5' untranslated region furthermore contains a dimer linkage domain responsible for the dimerization of the two viral genomes in the virion. Immediately upstream from the U3 region is another important cis-element, the polypurine tract (PP), which consists of a stretch of A and G residues. This element serves as a site for priming plus-strand DNA synthesis during reverse transcription.

2. The retroviral lifecycle

The retroviral lifecycle is outlined in FIG. 4. Two different mechanisms have been proposed to explain the entry of the virus particle into the host cytoplasm. Most retroviruses, including MLV, are thought to enter the host cell through receptor-mediated endocytosis, a process in which the whole enveloped virus particle is internalized into an endosomal body. The receptor molecule for the ecotropic murine leukemia viruses has been cloned and identified as a cationic amino acid transporter.

After the viral core particle has entered the cytoplasm of the host cell, all enzymatic functions leading to the integrated double-stranded DNA provirus are managed by viral proteins synthesized in the previous host cell and brought along in the virion. The fate of the viral proteins after entry of the core particle is not clear, but the reverse transcriptase, the integrase and the capsid protein remain with the RNA genome forming the nucleoprotein complex in which reverse transcription occurs. Recently, also the matrix protein has been found in association with the nucleoprotein complex.

Following reverse transcription, the nucleoprotein complex migrates to the host cell nucleus. The mechanism responsible for the nuclear localization is unclear, although evidence from Rous sarcoma virus (RSV) suggests the IN protein to be important since the RSV IN protein, when produced in mammalian cells, is localized in the nucleus. Entry of the nucleoprotein complex into the nucleus requires mitosis, probably because the nucleoprotein complex cannot penetrate the nuclear envelope. Once in the nucleus, integration is mediated by the IN protein. The IN protein recognizes the conserved inverted repeats at the ends of the LTRs and removes 2 bases from the 3' hydroxyl termini of both strands. The IN protein also catalyzes a cleavage in the host DNA and mediates the connections between the proviral DNA and the host DNA. As for the specificity of integration no consensus host DNA target sequence has been found, although a tendency to integrate near DNase I-hypersensitive sites has been reported.

For the simple retroviruses (including MLV) transcription and translation is performed by the host cell machinery. Complex viruses (including HIV and HTLV) encode trans-activating proteins involved in transcriptional regulation. The assembly of MLV particles takes place at the host membrane, and the process coincides with the budding process. In mammalian B and C type viruses (MMTV and HTLV, respectively) viral core particles are assembled in the host cell cytoplasm. Encapsidation of the viral genomic RNA is mediated through binding of the cis-acting encapsidation signal and the NC moiety of the Gag- or the Gag-Pol precursor protein.

After budding, the Gag- and Gag-Pol polyproteins are cleaved by viral protease (PR). Maturation of the viral proteins results in an overall change in virion morphology. In addition to proteolytic cleavage of the viral polyproteins following budding, the genomic RNA also undergoes a maturation process resulting in a compact dimeric genome.

3. Reverse transcription

The enzyme reverse transcriptase was discovered in 1970, and the current model of reverse transcription was proposed in 1979 (Gilboa et al. 1979). In addition to a DNA polymerase that can copy either RNA or DNA templates, reverse transcriptase contains an RNase H which selectively degrades RNA in RNA/DNA hybrids.

Retroviruses utilize a cellular tRNA molecule as a primer during reverse transcription. Different retroviruses utilize different tRNA species as primers in reverse transcription. Murine leukemia viruses (MLVs) and human T-cell leukemia virus (HTLV) use a proline-tRNA primer, human immunodeficiency virus (HIV) and mouse mammary tumor virus (MMTV) utilize a lysine-tRNA primer, whereas avian leukosis sarcoma virus (ALSV) use a tryptophan-tRNA molecule as a primer for reverse transcription. However, within a given group of retroviruses, the sequence of the primer binding site is highly conserved during retroviral replication, where the 3' 18 nucleotides of the tRNA molecule are copied during plus-strand synthesis. Furthermore, during the viral life cycle the tRNA primer is likely to specifically interact with viral proteins and the viral genome during the processes of packaging, annealing, and reverse transcription. Specific interactions between the tRNA primer and the viral proteins reverse transcriptase and the nucleocapsid protein, as well a secondary interactions between the tRNA and viral genomic RNA have been demonstrated in several viruses.

In a recent article (Lund et al. 1993) the present inventors have altered the MLV wild-type PBS matching a proline-tRNA to sequences matching either a glutamine- or a lysine-tRNA. The effect of the altered PBS sequences was studied by single cycle replication of a retroviral vector, enabling them to quantify the effect of the introduced mutations. The structure of the transduced PBSs was analyzed by amplification of proviral vectors followed by direct sequencing of the PBS and surrounding DNA. They found that MLV can replicate by using various tRNA molecules as primers and concluded that primer binding site-tRNA primer interactions are of major importance for tRNA primer selection, but that efficient primer selection does not require perfect Watson-Crick base pairing at all 18 positions of the primer binding site. Later they have proved that MLV can also replicate by using the methionine (initiator)-tRNA as the primer.

The tRNA primer is packaged in the virion during virus assembly, and originates therefore from the previous host cell. The tRNA primer molecule interacts through base pairing with a region of the genomic RNA (the primer binding site) situated downstream from the U5 region at the 5' end of the genome (FIG. 5). In murine leukemia viruses 18 bases from the aminoacceptor stem and the TΨC loop of the tRNA are annealed to the PBS and the reverse transcription of the retroviral genome is initiated from the 3' end of the tRNA molecule. From here reverse transcriptase synthesizes the first DNA, the minus-strand strong stop DNA. The 3' end of the minus-strand strong stop DNA contains a copy of the R region complementary to the 3' R region of the genomic RNA. The newly synthesized DNA is thought to relocate to this region (first jump) from where minus-strand DNA synthesis can proceed. As the growing minus-strand is synthesized, RNase H continues to degrade the viral RNA. A fragment of the viral RNA, situated at the polypurine tract (PP), is left and acts as the primer for plus-strand DNA synthesis. Plus-strand DNA synthesis proceeds through U3, R and U5 and copies the bases of the tRNA molecule that are complementary to the PBS. At position 57 in the tRNA molecule the reverse transcriptase encounters a modified nucleotide ($m^1A$), which it presumably cannot use as a template, and synthesis of the plus-strand terminates. RNase H removes the overhanging part of the tRNA molecule. The remaining part of the plus-strand, leading to the complete double-stranded DNA provirus, is primed by the first part after a relocation event where the two complementary copies of the PBS interact through base pairing. Resulting from this complex reaction is a double-stranded DNA provirus, which is longer than the RNA template due to the copying of repetitive sequences U3 and U5.

4. Retroviral vector systems

A central element in this invention is a retroviral vector propagation system in which infectious, recombinant virus particles can be produced without contamination with replication competent wild type virus. The main advantage of retroviral vectors is the utilization of the efficient infection and integration processes developed in the viruses through evolution.

The proviral genome of MLV can be divided into sequences that are required in cis or in trans for viral replication (FIG. 6). The cis-acting elements are located at the ends of the proviral genome and encompass the U3, R and U5 regions, the inverted repeats in U3 and U5, the PBS, the polypurine tract and the packaging signal. These sequences contain all the elements needed for correct reverse transcription and integration and make up the minimal requirements for a retroviral vector. The space needed for the insertion of foreign DNA is created by deleting the sequences encompassing the open reading frames gag, pol and env.

For most applications it is essential that the retroviral vectors used for gene transfer are unable to generate new virus progeny in the target cell. This requires that the vector constructs are replication defective, the components required to complete the life cycle being supplied from loci outside the vector construct in the virus producing cell.

If these components are not present in the target cell, further virus generation is not possible. However, replication competent viruses may arise as a result of recombination. Such virus may eventually have pathological consequences including the malignant transformation of the infected target cell.

Retroviral vectors are normally propagated by the use of specialized packaging cell lines. In such packaging cell lines all trans-acting virus-encoded components are produced from loci outside the vector construct.

The first packaging cell line was constructed by Mann et al. (1983). This cell line (Ψ-2), containing a Moloney-MLV proviral genome with a 350 bp deletion overlapping the packaging signal, produces all the viral proteins needed in trans for virion production (FIG. 7A). After transfection into this cell line, retroviral vectors carrying the necessary cis-signals will be packaged into infectious virions (FIG. 7B). Although the early packaging cell lines Ψ-2 (Mann et al. 1983) and Ψ-AM[1] (Cone & Mulligan 1984) have been used successfully in a large number of studies, they suffer from important deficiencies. Despite the deletion of the packaging signal replication competent viruses may arise, presumably as a result of recombination between the packaging construct and introduced vector sequences or viruses endogenous to the genome of the packaging cell (Miller 1990). Recombination occurs at high frequency in retroviral replication. The rate of homologous recombination between two heterologous genomes packaged in the same virion has been estimated to range as high as 10 to 30 % for each round of replication. A number of studies have reported recombination between introduced viruses or vectors and homologous sequences endogenous to the host cell. Further evidence that deletion of the packaging signal is not sufficient to prevent packaging, comes from a study of a retroviral vector without a packaging signal where packaging and transfer of this vector was easily detected, even though the transduction rate was 3000 fold lower than that of a vector containing the packaging signal. Obviously, the 350 bp deletion in the 5' untranslated region does not inhibit packaging, a fact supported by reports indicating that sequences within the gag open reading frame and within the U5 region also may play a role in the encapsidation process. Furthermore, retroviral particles also package non-viral RNA, indicating that both specific recognition and a more general affinity for RNA is involved in the encapsidation process. Moreover, only a single recombination event is needed to restore the packaging signal and regenerate replication competent viruses. There are several reports of helper virus regeneration resulting from homologous recombination between the packaging construct and either introduced vectors or endogenous viral sequences.

[1] The Ψ-AM packaging construct resembles Ψ-2 but expresses another env gene giving rise to recombinant viruses with an amphotropic host range.

To further reduce the risk of generation of complete viruses by recombination in the packaging cells, second generation pakcaging cell lines have been constructed. The main advantage of these new packaging cell lines is that the packaging construct has been divided into two separate constructs; one encoding the gag-pol polyprotein and one carrying the env gene (FIG. 8). By splitting the packaging construct the risk of recombination is greatly reduced (Miller 1990). By reducing the sequence homology of the packaging construct to the introduced vectors and endogenous MLV-like sequences the risk of homologous recombination can be further reduced.

However, not only the engineered parts of the packaging cells but also endogenous retroviral sequences in the DNA of the packaging cell as well as in the target cell may have to be considered in safety assessments. The risk of a contribution from endogenous retroviruses may be reduced by use of packaging cells based upon cell lines from other species where the endogenous retroviral elements may be more divergent. The current packaging cell technology has recently been reviewed (D. Valerio 1992).

A recent publication (Chapman et al. 1992) describes that the yeast retrotransposon Tyl uses $tRNA_i^{Met}$ as a primer for Tyl reverse transcription, and that mutations in the Tyl element that alter 5 of the 10 nucleotides that are complementary to the $tRNA_i^{Met}$ abolish Tyl transposition. When a yeast strain is constructed which lacks wild-type $tRNA_i^{Met}$ and is dependent on a mutant derivative of $tRNA_i^{Met}$ that has an altered acceptor stem sequence, engineered to restore homology with the Tyl-PBS mutant, the compensatory mutations made in the $tRNA_i^{Met}$ alleviate the transposition defect of the Tyl-PBS mutant. The mutant and wild-type $tRNA_i^{Met}$ are enriched within Tyl virus-like particles irrespective of complementarity to the Tyl-PBS, and from this the authors conclude that complementarity between the Tyl-PBS and $tRNA_i^{Met}$ is essential for transposition, but is not necessary for packaging of the tRNA inside virus-like particles.

SUMMARY OF THE INVENTION

To further reduce the risk of uncontrolled regeneration of complete virus or for other means of vector spread resulting from an interaction of a retroviral vector with various engineered or endogenous cis- or trans-acting components, the present invention proposes to make the vector transfer dependent upon a specifically engineered, tRNA-like primer for reverse transcription. Thus, in principle, only specialized packaging cells provided with an appropriate artificial primer would allow vector propagation (FIG. 9).

Another aspect of this invention is the potential use of retroviral vectors as antiviral agents. Such vectors may be directed against pathogenic viruses related to the type used for construction of the vector, thus having the same host range and cellular tropism. This strategy may turn out to be of particular importance for antiviral approaches towards HIV or HTLV-1. A key point in this strategy is to direct antiviral activity against critical cis-acting genetic regions of the pathogenic virus e.g. by antisense or ribozyme constructs. The primer binding site (PBS) is an important and conserved cis region and therefore constitutes a possible target site. Retroviral vectors utilizing an artificial reverse transcription primer and hence carrying a modified PBS would be particularly advantageous, since the antiviral activity of such vectors would not be directed towards their own cis elements.

As mentioned above, all retroviruses require a specific tRNA primer for reverse transcription; however different groups of retroviruses may use different tRNA species. The tRNA-primer usually interacts with a complementary sequence, the primer binding site (PBS) near the 5' end of the viral genomic RNA. We have addressed the possibility of using an artificial tRNA-like primer for transmission of vectors derived from murine leukemia viruses (MLVs). Most available retroviral systems were derived from this group of viruses and all approved clinical protocols for gene therapy or gene marking by retroviral vectors use vectors based upon this specific group. The tRNA utilized as a primer for reverse transcription by MLV is a proline-specific tRNA ($tRNA^{pro1}$ or $tRNA^{pro2}$) that interacts with a complementary 18 nucleotides PBS-sequence in the retroviral genomic RNA.

Accordingly, the present invention provides a retroviral vector comprising a retrovirus with infectivity for birds and/or mammals in which at least part of the genomic RNA sequences carrying information for the production of viral proteins required in trans for retroviral replication have been replaced by one or more sequences carrying information to be introduced in a target cell chromosome, said retroviral vector being characterized in that the primer binding site (PBS) has been modified to a sequence that does not allow strong base pairing with the 3' end or other priming sequence in any naturally occurring tRNA.

By "strong base pairing" is meant a degree of binding that allows priming of a complementary DNA strand in the reverse transcription of the vector RNA. A sequence that does not allow strong base pairing should preferably show less than 50% homology, and more preferably less than 33% homology, with the 3' end or other priming sequence in any naturally occurring tRNA.

A suitable retroviral vector according to the invention is derived from murine leukemia virus (MLV) as described above; and in a specific vector of this kind the primer binding site (PBS) has been modified to the sequence stated in the following SEQ ID No. 1 UGGGAUGAAUCUAGG-GAU.

To further reduce the possibility of binding of naturally occurring tRNA molecules to modified primer binding sites it may be advantageous to alter the three 5' nucleotides (UGG) of the PBS thereby removing any complementarity to the 3' CCA-tail of naturally occurring tRNA molecules.

In a retroviral vector according to the invention, especially in one derived from murine leukemia virus (MLV), it may be advantageous also to modify up to 5 nucleotides 3' of the primer binding site to a sequence that does not allow additional base pairing with a tRNA primer.

The invention also provides a replication system for the retroviral vector according to the invention, said system comprising a tRNA-like primer for reverse transcription of the retroviral vector as well as a DNA sequence comprising the structural gene sequence of said primer which is incorporated in a packaging cell line for viral replication of the retroviral vector.

A tRNA-like primer according to the invention is derived from a tRNA priming the reverse transcription of the retrovirus, from which the vector is derived, by modifying the 3' end or other sequence thereof, which is to be active in priming, to a sequence that allows strong base-pairing with the PBS of the vector.

In such a tRNA-like primer it may be necessary or advantageous that also sequences involved in forming the secondary clover-leaf structure of the tRNA molecule by internal base-pairing with the modified sequences are modified to be complementary therewith.

If the three 5' nucleotides in the PBS of a retroviral vector have been altered to remove any complementarity to the 3' CCA-tail of naturally occurring tRNA molecules, it may be necessary or advantageous to alter the CCA-tail in a tRNA-like primer according to the invention to be complementary to the altered PBS in order to optimize the system with respect to efficiency of transfer.

Specific tRNA-like primers according to the invention, which are able to prime the reverse transcription of a retroviral vector derived from murine leukemia virus, are derived from tRNA$^{pro}$, tRNA$^{gln1}$, tRNA$^{lys3}$ or tRNA$^{met(i)}$, in particular from tRNA$^{pro}$.

A DNA sequence according to the invention comprises the structural gene sequence of a tRNA-like primer as described above.

A suitable such DNA sequence is a synthesized oligonucleotide designed as a mutated version of the murine tRNA$^{pro}$ gene and containing, besides the the structural sequence, a 5' leader sequence and a 3' sequence encompassing the termination signal (TTTTT), corresponding to the flanking sequences of the murine gene; and a specific DNA sequence of this kind has the sequence stated in SEQ ID No. 2 as illustrated in FIG. 10.

A packaging cell line according to the invention is an avian or mammalian cell line which has been transformed by the insertion of one or more vectors comprising the DNA sequences carrying information for the production of viral proteins required in trans for retroviral replication, and which is characterized in that it has also been transformed by the insertion of a vector comprising a DNA sequence as described above.

A suitable packaging cell line is derived from a murine cell line.

Also, a suitable packaging cell line may be derived from any cell line supporting MLV production. Packaging cell lines derived from non-murine cell lines may exhibit a reduced risc of recombination between vector constructs, packaging constructs and endogenous retroviruses.

Finally, the present invention also provides avian or mammalian cells which have been transfected with a retroviral vector according to the invention.

The legend identifies individual proteins found in the mature virion. The two genomic RNAs are dimerized near the 5' end and are here shown partly covered by NC protein. (From Whitcomb & Hughes, 1992)

Figure 1:
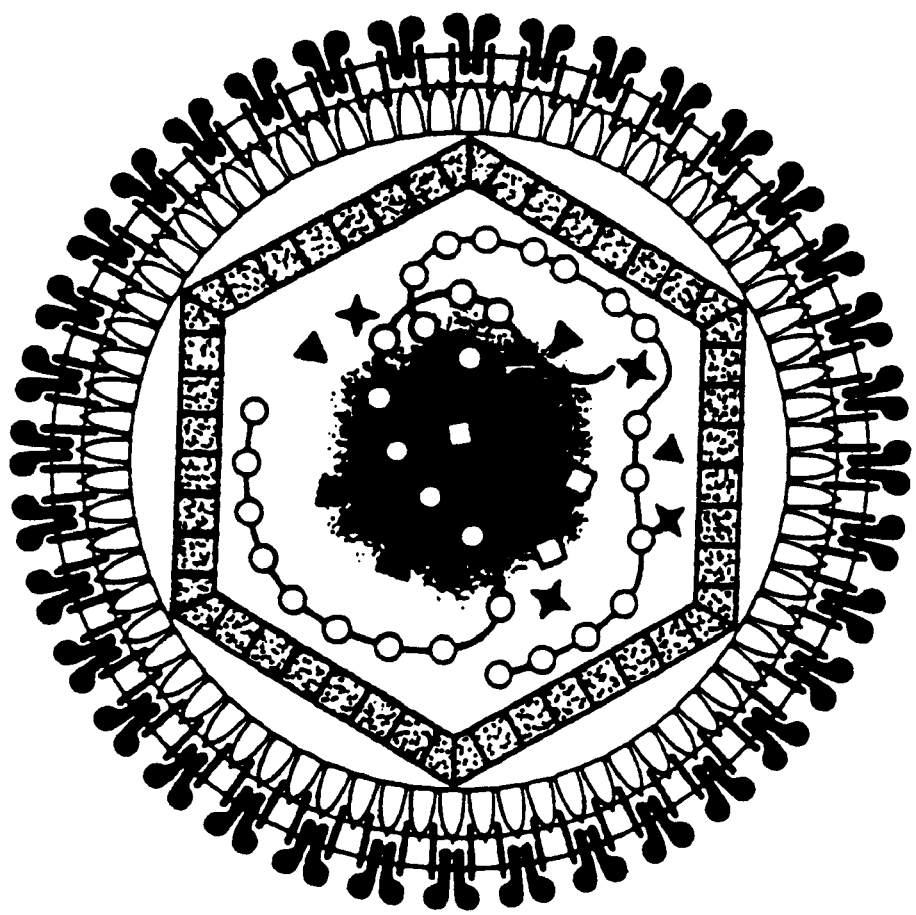
FIG. 1: A diagrammatic outline of a murine leukemia virus (MLV) particle.
Figure 2:
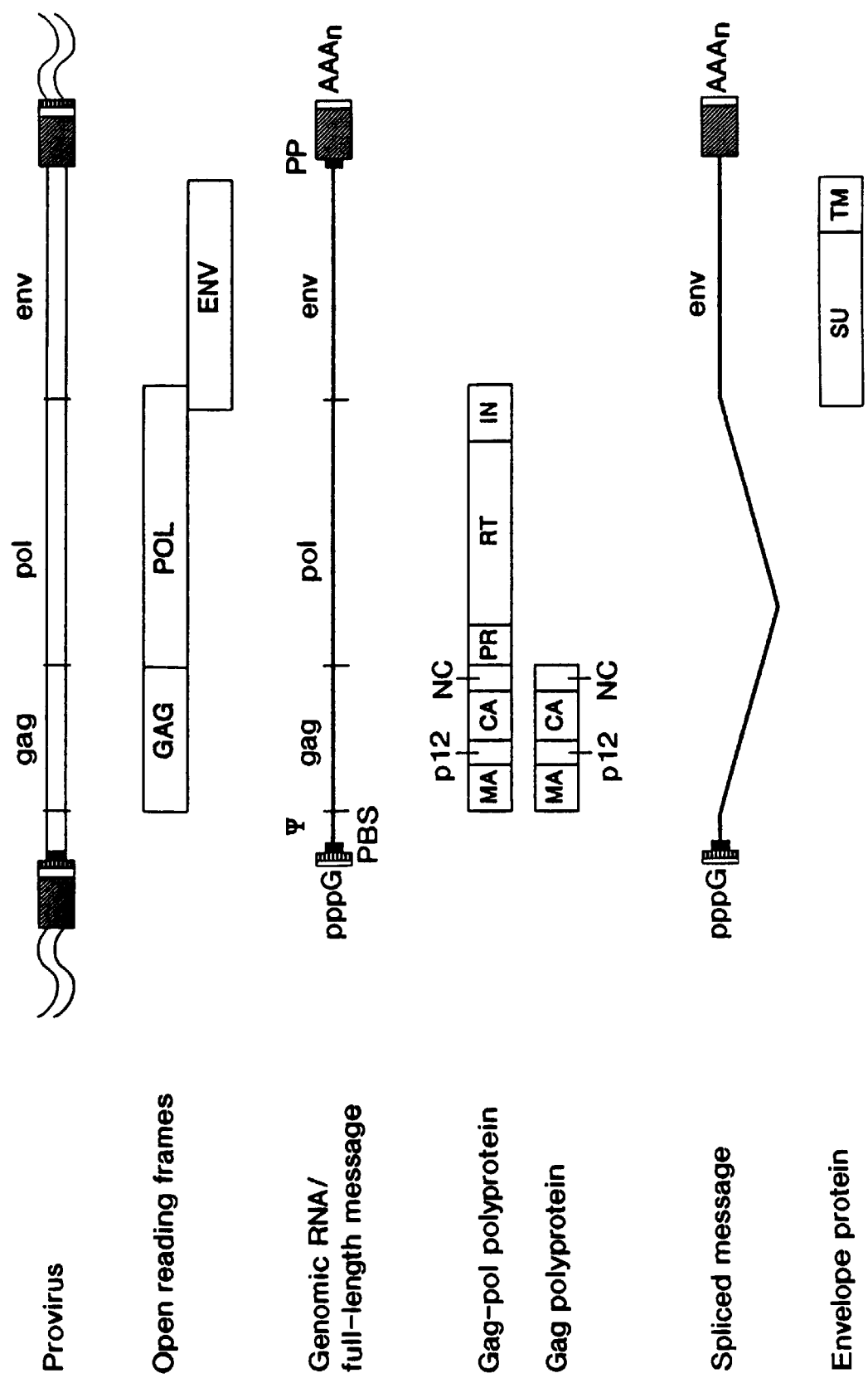

FIG. 2: The genomic map of murine leukemia virus (MLV).

At the top the structure of the integrated provirus followed by the open reading frames. The provirus gives rise to two MRNA transcripts. The full length MRNA encodes the Gag- and the Gag-Pol polyproteins and also serves as the genomic RNA, while a spliced mRNA encodes the two envelope proteins SU and TM. The subdivision of the Gag- and Gag-Pol polyproteins into functional domains representing the mature virion proteins is also shown. (Adapted from Whitcomb & Hughes, 1992)

Figure 3:
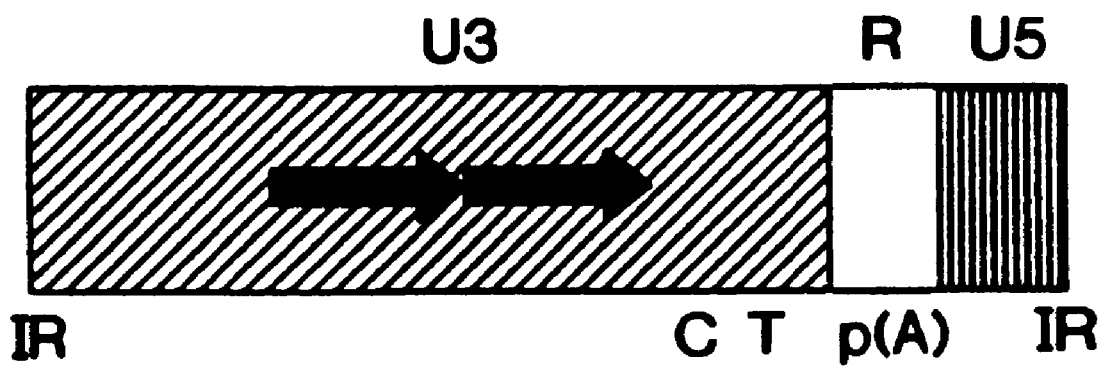

FIG. 3: The structure of the Akv-MLV LTR.

The arrows in U3 represent the two enhancer direct repeats, IR: inverted repeat, C: CAAT-box, T: TATA-box, p(A): polyadenylation signal.

Figure 4:
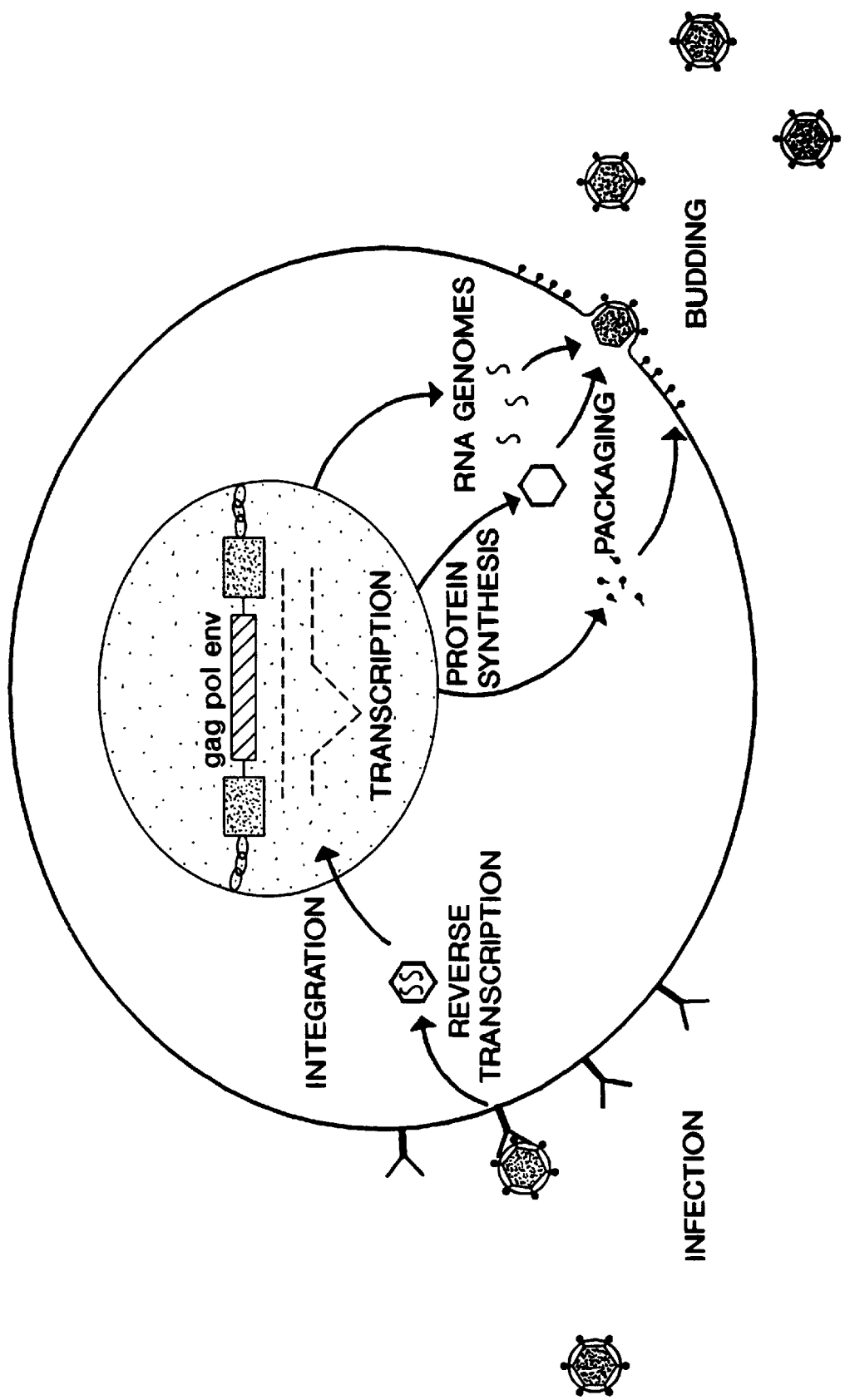

FIG. 4: The retroviral lifecycle.

Going from left to right; a schematic outline of the lifecycle of MLV. The virus particle enters the host cell through interaction with a specific receptor molecule. Reverse transcription is completed in the cytoplasm before the DNA/protein complex containing the viral DNA migrates to the nucleus where the provirus is integrated into the host genome. Transcription of the provirus and translation of the viral mRNA is carried out by the host cell machinery. New virus particles are formed at the cell surface.

Figure 5:
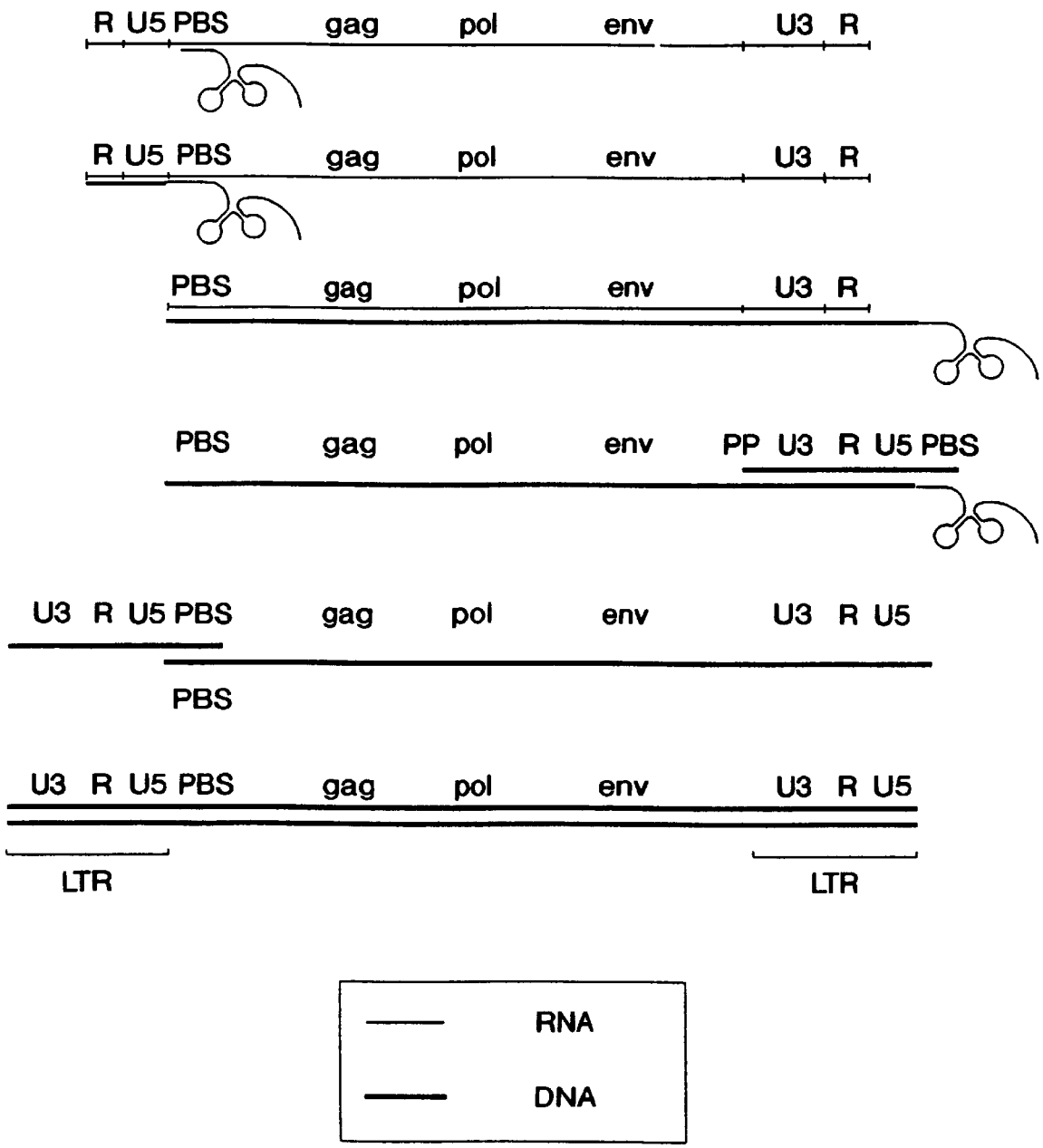

FIG. 5: A model of reverse transcription.

From top to bottom the steps leading from a single-stranded positive sense mRNA to the double-stranded DNA provirus are shown. Thin lines represent RNA, and thick lines represent DNA.

FIG. 6: Schematic representations of the proviral genome of MLV and of a MLV-based retroviral vector.

Upper) Division of a MLV proviral genome into sequences required in cis or in trans for retroviral replication.

Lower) The basic configuration of a retroviral vector; the gene of interest is inserted between the two LTRs instead of the coding sequences which are provided in trans by the packaging cell line.

Figure 7B:
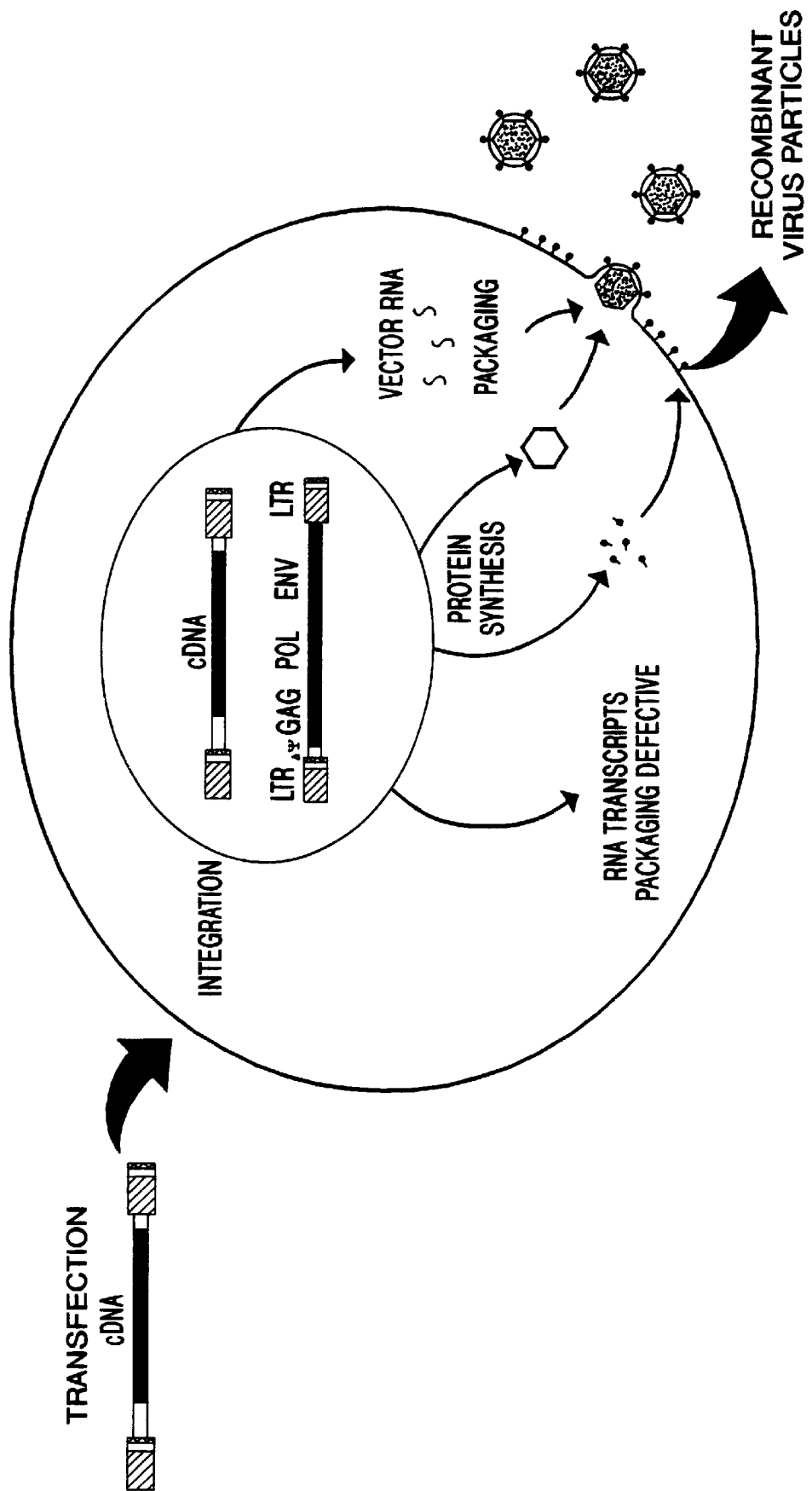

FIGS. 7A and 7B: Retroviral packaging system.

7A) A retroviral packaging cell containing a simple packaging construct which is able to produce the viral proteins but, due to a deletion in the packaging signal, is packaging defective.

7B) The RNA of a retroviral vector introduced into a packaging cell will be efficiently encapsidated in recombinant viral particles.

FIG. 8: Retroviral packaging constructs.

Top: A simple packaging construct lacking the packaging signal (Ψ-2, Ψ-AM).

Bottom: An advanced packaging construct split into two separate units. The retroviral promoter-enhancer region has been substituted by a heterologous promoter (e.g. the cytomegalovirus promoter), and the polyadenylation signal has been replaced with another (e.g. from SV 40).

Figure 9:
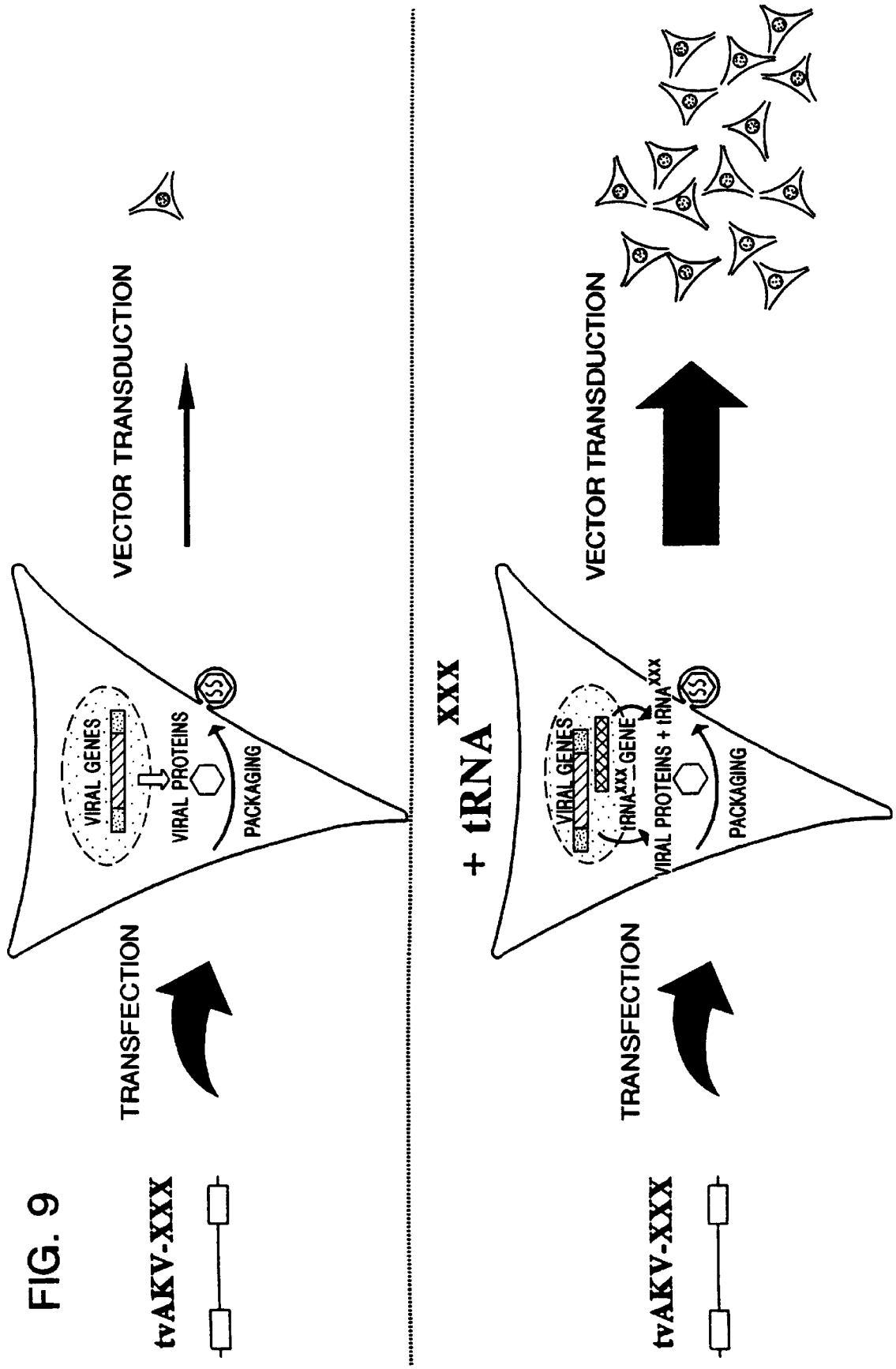

FIG. 9: The basic idea of making vector transfer dependent upon the presence of an artificial RNA primer.

Upper panel: A packaging cell without the artificial primer, from where transmission of the vector with the mutated primer binding site (tvAkv-XXX) is not possible.

Lower panel: A packaging cell complemented with a synthetic gene encoding an artificial RNA primer. The RNA primer ($tRNA^{xxx}$) matches the primer binding site in tvAKV-XXX and allows efficient transmission of this vector.

Figure 10:
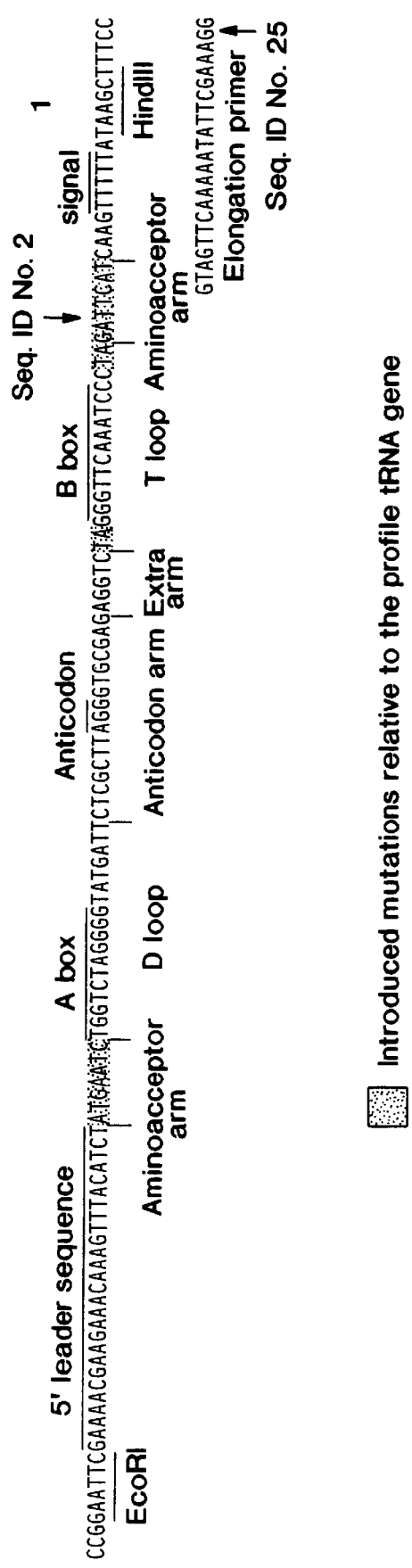

FIG. 10: Complete sequence of the synthetic $tRNA^{xxx}$ gene SEQ ID NO. 2.

The gene was designed on the basis of the sequence for the mouse gene for $tRNA^{pro1}$. The functional regions of the normal gene and the introduced mutations are indicated. One 127 nucleotides long oligonucleotide was synthesized and made double stranded by elongation from an elongation primer SEQ ID NO. 25. The double stranded product was cloned into plasmid vector pUC19. Plasmid DNA was transfected into Ψ-2 packaging cells.

FIG. 11: Vector recombination with endogenous MLV-like sequences.

Hypothetical model of recombination between PBS-xxx and MLV-like sequences harbouring a PBS-gln2. Recombination is most likely to occur during minus-strand DNA synthesis. Minus strand strong stop DNA is indicated by a thick line, RNA is depicted by thin lines, and possible recombination-crosses are shown as dotted lines.

FIG. 12: Primer binding site (PBS) generation in rare transduction events.

Hypothetical model explaining the rare transductions of PBS-xxx and PBS-pro.

a) Normal priming of DNA synthesis after the second strand transfer event. PBS(t) is a DNA copy of the 3' 18 nucleotides from the primer molecule. PBS(g) is the DNA copy of the genomic primer binding site.

b) Imperfect binding of tRNA primer to PBS-xxx resulting in 3' mismatch after second strand transfer. Removal of 3' overhang by cellular exonucleases restores priming ability and regenerates PBS(g), i.e. PBS-xxx.

c) PBS-pro may be regenerated from PBS-xxx provided the copying of the tRNA primer molecule into DNA has extended beyond the methylated adenosine residue at position 19 from the 3' end of the tRNA molecule (tRNA read-through).

DETAILED DESCRIPTION OF THE INVENTION

When testing the significance of the tRNA primer molecule in the viral life cycle of a retroviral vector in a retroviral vector propagation system, the effect of the introduced mutations can be quantified by measuring vector transduction efficiency. Furthermore, using a vector harboring the selectable marker-gene neo (Beck et al. 1982), conferring resistance to the neomycin analog G418, individual transduction events can be examined by analyzing the structure of transduced proviruses after 1 round of retroviral replication.

According to the present invention the PBS of an Akv-MVL-based retroviral vector was modified to a sequence (PBS-xxx) that does not allow strong base-pairing with the 3' end of any known murine tRNA molecule. PBS-xxx was designed on the basis of an alignment of the published murine tRNA sequences (see Table) so that the PBS-xxx sequence is complementary to an 18 nucleotides RNA sequence showing the least possible homology to the 3' ends of these tRNA molecules. However, as the transcription and maturation pathway of eukaryotic tRNA molecules provides all tRNAs with a 3' CCA-tail, the 5' UGG sequence of the PBS was not modified in order to preserve complementarity with an artificial tRNA-like primer retaining the CCA-tail as described below. The chosen RNA sequence was the following: AUCCCUAGAUUCAUCCCA SEQ ID NO. 24; and accordingly PBS-xxx has the complementary sequence stated in SEQ ID No. 1 UGGGAUGAAUCUAGGGAU.

TABLE

| tRNA | 3' 18 nucleotides | | GenBank/EMBL Accession number |
|---|---|---|---|
| Ala (g) | UCCCCGGCAUCUCCACCA | SEQ ID NO: 3 | MMTGPA1 |
| Arg | CUCCUGGCUGGCUCGCCA | SEQ ID NO: 4 | MMRL1 |
| Asp (g) | UUCCCCGACGGGGAGCCA | SEQ ID NO: 5 | MMRNO3 |
| Cys (g) | AUCCAGGUGCCCCCUCCA | SEQ ID NO: 6 | MMTGCI |
| Gln-1 | AUCUCGGUGGGACCUCCA | SEQ ID NO: 7 | MMTROA |
| Gln-2 | AUCUCGGUGGAACCUCCA | SEQ ID NO: 8 | [a] |
| Glu | UUCCCGGUCAGGGAACCA | SEQ ID NO: 9 | [a] |
| Glu (g) | UUCUCGGUCAGGGAACCA | SEQ ID NO: 10 | MMRNO3 |
| Gly (g) | UUCCCGGCCAACGCACCA | SEQ ID NO: 11 | MMRNO3 |
| His (g) | AUCCGAGUCACGGCACCA | SEQ ID NO: 12 | MMTMT1 |
| Ile | UCCCCGUACGGGCCACCA | SEQ ID NO: 13 | [a] |
| Lys (g) | GUCCCUGUUCAGGCGCCA | SEQ ID NO: 14 | MMRNO1 |
| Lys-3 | GCCCCACGUUGGGCGCCA | SEQ ID NO: 15 | MMK4 |

TABLE-continued

| tRNA | 3' 18 nucleotides | | GenBank/EMBL Accession number |
|---|---|---|---|
| Met(i) | AACCAUCCUCUGCUACCA | SEQ ID NO: 16 | MMMI |
| Met | ACCUCAGAGGGGCACCA | SEQ ID NO: 17 | MMTRNM3 |
| Met | UCCUCACACGGGGCACCA | SEQ ID NO: 18 | MMM4 |
| Phe | UCCCGGGUUUCGGCACCA | SEQ ID NO: 19 | MMF |
| Pro | AUCCCGGACGAGCCCCCA | SEQ ID NO: 20 | MMP1 |
| Ser | UCCACCUUUCGGGCGCCA | SEQ ID NO: 21 | a |
| Trp | AUCACGUCGGGGUCACCA | SEQ ID NO: 22 | TNTMS |
| Val | AACCGGGCGGAAACACCA | SEQ ID NO: 23 | MMV1MI | a Sequences from Sprintzl etal.(1989). Nucleic Acids Research, 17: Supplement r1–r172.
(g): Derived from sequence of tRNA gene.

The mutations were introduced into the PBS of the Akv-MLV-based retroviral vector, tvAkv-neo[2] (Paludan et al. 1989), using polymerase chain reaction (PCR) -mediated site-directed mutagenesis. A two-step PCR procedure was employed for changing the PBS-pro of tvAkv-neo to PBS-xxx and to amplify the full-length transmission vector. The first step involved two sub-reactions: The reaction amplifying the 5' part of the vector introduced the desired mutations and added a specific linker sequence to the upstream LTR; the reaction amplifying the 3' part created a small overlap with the upstream fragment and added a linker sequence to the down-stream LTR. The second PCR reaction used primers matching the introduced linkers of the upstream and downstream LTRs to amplify the complete 3.4 kb vector. Unique EcoRI and XhoI restriction sites present in the linkers were used for cloning of the modified vectors in the E. coli plasmid pUC19. The structure of the resulting plasmid clones was verified by sequence analysis of the PBS and surrounding region and by restriction analysis. The functional state of the neo gene was confirmed by the ability of the plasmids to confer kanamycin resistance upon recipient bacteria. For further details on the experimental procedure see Lund et al. 1993.

[2] tv: transmission vector

DNA of this vector was transferred into the Ψ-2 packaging cell line (Mann et al. 1983) and recipient packaging cells were selected by growth in geneticin (G418). Supernatant from this culture was used to infect NIH 3T3 cells and the vector titre determined from the number G418 resistant colonies resulting from the infected population of NIH 3T3 cells exactly as described previously (Lund et al. 1993). The titre was reduced by a factor of $10^5$, relative to a parallel experiment with the parent vector carrying the normal PBS-sequence. The transduction titres were $5.2 \times 10^6/4.3 \times 10^6$ for the vector with the wild type PBS and $7.6 \times 10^1/5.4 \times 10^1$ for the PBS-xxx vector (duplicate determinations for each).

Figure 11:
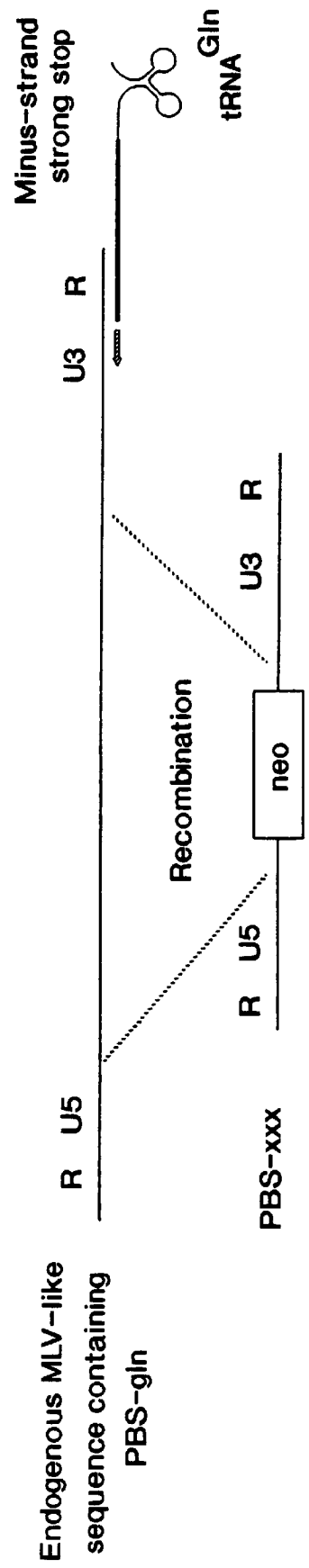
Figure 12A:
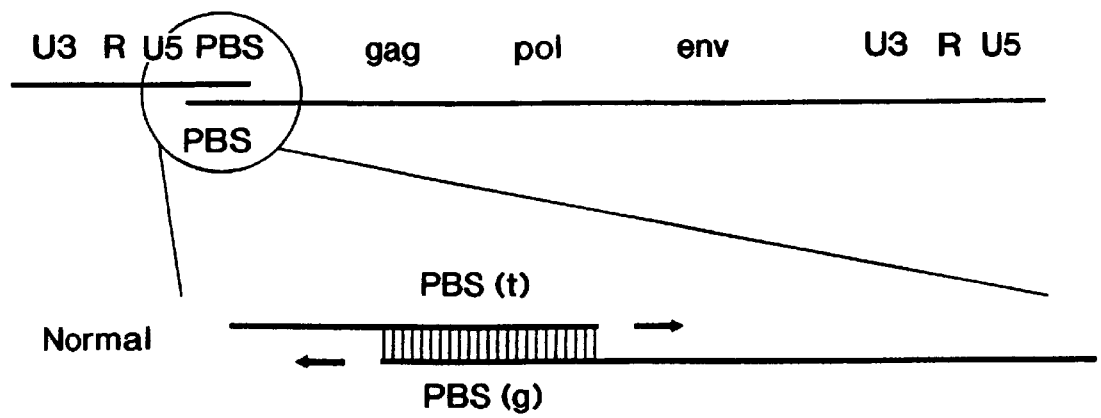
Figure 12B:
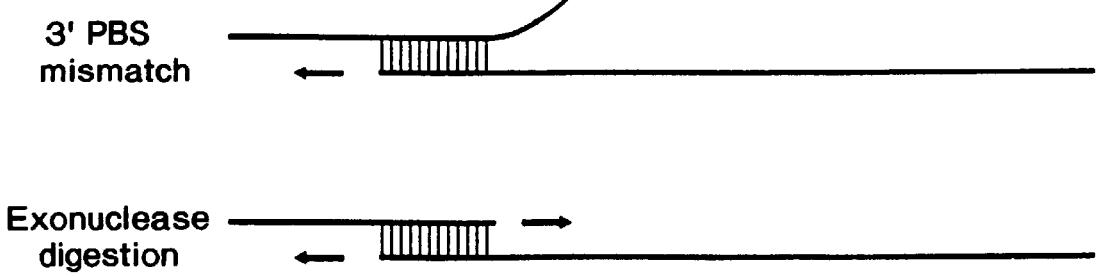
Figure 12C:
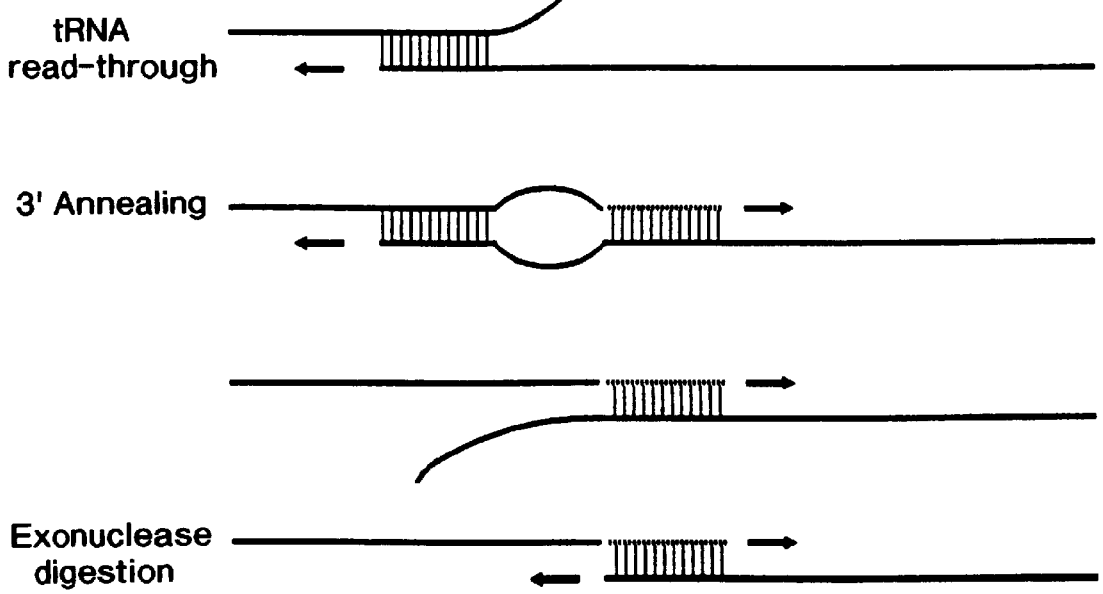

Sequence analysis of rare PBS-xxx transduction events showed that three different PBSs had been transduced; PBS-xxx, PBS-pro and PBS-gln. Examination of nucleotide sequences flanking the transduced PBSs matching a glutamine tRNA revealed a pattern of mutations indicating that these PBSs had originated from homologous recombination with endogenous MLV-like sequences rather than from the binding of a glutamine tRNA to PBS-xxx. Furthermore, the PBS-gln2 flanking sequences are identical to endogenous MLV-like sequences reported by Nikbakht et al. (1985). Therefore, it can be concluded that PBSs matching tRNA$^{gln2}$ originate from recombination events between the introduced PBS-xxx vector and endogenous MLV-like sequences (FIG. 11). Ten of the analyzed clones resulting from rare PBS-xxx transduction events carried the PBS-xxx originating from the introduced vector, and 3/26 colonies had a PBS matching tRNA$^{pro}$. The generation of these transduced PBSs cannot be directly explained by the model for reverse transcription. However, the results can be explained asssuming weak interactions between a tRNA$^{pro}$ and PBS-xxx. PBS-xxx could be regenerated, if tRNA$^{pro}$ primed reverse transcription from the CCA-tail only, and endogenous exonuclease activity removed the resulting 5' overhang after the second jump (FIG. 12b). Regeneration of PBS-pro requires erroneous read-through of the primer tRNA molecule beyond the 18th 3' nucleotide creating a stretch of 5 nucleotides complementary to a sequence immediately downstream from the primer binding site. In Akv-MLV tRNA read-through creates a stretch of 5 nucleotides complementary to a sequence motif downstream from the PBS. Annealing to this 3' sequence is thought to induce instability due to the number of unpaired bases, and a resulting 5' PBS mismatch may be removed by exonuclease activity leading to the generation of PBS-pro. (FIG. 12c).

We next attempted to complement the transduction deficiency of PBS-xxx by providing Ψ-2 packaging cells with a modified tRNA that would give a good match to PBS-xxx. A gene, putatively encoding a tRNA-like primer with a 3' end matching PBS-xxx was built from chemically synthesized oligonucleotides. This gene ("the tRNA$^{xxx}$ gene") was designed on the basis of the mouse gene for tRNA$^{pro1}$ (Russo et al. 1986) (FIG. 10) by introduction of 18 mutations. The gene was designed to maintain the signals for transcription and processing of this tRNA. Ψ-2 cells were transfected with DNA for this artificial gene together with a selectable hygromycin B encoding marker gene. Cells carrying stably integrated copies of the tRNA$^{xxx}$ gene were generated by growth in hygromycin B containing medium. These cells were transfected with DNA from the PBS-xxx vector and the titre of functional vector particles determined under transient expression conditions to be 2.3 $10^5$ c.f.u./ml.

This titre is in the same range as that observed under transient expression conditions with the isogenic vector carrying the normal PBS. Usually transfer efficiencies observed after stable transfection of vector DNA are about 10 times higher than those observed after transient transfer, where only a fraction of the cells have received vector DNA. Additional characterization of the system will involve determination of transfer efficiencies after stable transfer.

4. What are the advantages of the new solution?

Our results thus indicate that impairment of the primer binding site by mutation reduces transfer efficiencies by a factor of $10^5$. However this transfer efficiency can be restored to normal levels by complementation with an engineered primer. This transfer principle may therefore combine efficient transfer from specifically engineered cells with severe limitations in the risk of spread under all natural conditions, where no primer matching PBS-xxx is expected to occur. In addition it may allow vector-mediated anti-viral activitiy directed against wild-type primer binding sites.

The technology may be further refined by alterations in the sequences of the modified primer binding site as well as in the artificial primer. In particular, changes corresponding to positions conserved in all tRNAs may be important. The RNA primer may be expressed under control of heterologous transcriptional regulatory elements to avoid dependence upon the intragenic polymerase 3 promoter sequences and to optimize transcript levels.

REFERENCES

Beck, E., E. A. Ludwig, R. Auerswald, B. Reiss, and H. Schaller (1982). Nucleotide sequence and exact location of the neomycin phosphotransferase gene from transposon Tn5. *Gene* 19: 327–336.

Chapman, K. B., A. S. Bystrom, and J. D. Boeke (1992). Initiator methionine tRNA is essential for Tyl transposition in yeast. *Proc. Natl. Acad. Sci. USA*. 89: 3236–3240.

Cone, R. D. & R. C. Mulligan (1984). High-efficiency gene transfer into mammalian cells: generation of helper-free recombinant retrovirus with broad mammalian host range. *Proc. Natl. Acad. Sci. USA*. 81: 6349–6353.

GenBank/EMBL Nucleotide Sequence Database.

Gilboa, E., S. W. Mitra, S. Goff, and D. Baltimore (1979). A detailed model of reverse transcription and tests of crucial aspects. *Cell* 18: 93–100.

Lund, A. H., M. Duch, J. Lovmand, P. Jørgensen, and F. Skou Pedersen (1993). Mutated Primer Binding Sites Interacting with Different tRNAs Allow Efficient Murine Leukemia Virus Replication. *Journal of Virology,* 67: 7125–7130.

Mann, R., R. C. Mulligan, and D. Baltimore (1983). Construction of a retrovirus packaging mutant and its use to produce helper free defective retroviruses. *Cell* 33:153–159.

Miller, A. D. (1990). Retroviral packaging cells. *Human Gene Therapy,* 1: 5–14.

Nikbakht, K. N., C.-Y. Ou, L. R. Boone, P. L. Glover, and W. K. Yang (1985). Nucleic sequence analysis of endogenous murine leukemia virus-related proviral clones reveals primer binding sites for glutamine-tRNA. *J. Vir.* 54: 889–893.

Paludan, K., H. Y. Dai, M. Duch, P. Jørgensen, N. O. Kjeldgaard, and F. S. Pedersen (1989). Different relative expression from two murine leukemia virus long terminal repeats in unintegrated transfected DNA and in integrated retroviral vector proviruses. *J. Vir.* 63: 5201–5207.

Russo, T., Costanzo, F., Oliva. A., Ammendola, R., Duilio, A., Esposito, F., and F. Cimino (1986). Structure and in vitro transcription of tRNA gene cluster containing the primers of MuLV reverse transcriptase. *Eur. J. Biochem.* 158: 437–442.

Sprintzl, M., T. Hartmann, J. Weber, J. Blank, and R. Zeidler (1989). Compilation of tRNA sequences and sequences of tRNA genes. *Nucleic Acids Res.* 17: rl–rl72 (Supplement).

Valerio, D., in "Transgenic Animals", Grosveld and Kollias, Eds., Academic Press, 1992.

Whitcomb, J. M. & S. H. Hughes (1992). Retroviral reverse transcription and interation: progress and problems. *Ann. Rev. Cell Biol.* 8: 275–306.

We claim:

1. A retroviral transfer vector comprising a retrovirus in which at least part of the genomic RNA sequences carrying information for the production of viral proteins required in trans for retroviral replication have been replaced by one or more sequences carrying information to be introduced in a target cell chromosome, where the primer binding site (PBS) has been modified to a sequence that does not allow strong base pairing with the 3' end of any naturally occurring tRNA, and where the three 5' nucleotides of the PBS are UGG.

2. A retroviral vector according to claim 1 in which the primer binding site (PBS) has been modified to a sequence showing less than 50% homology with the 3' end in any naturally occurring tRNA.

3. A retroviral vector according to claim 1 in which the primer binding site (PBS) has been modified to a sequence showing less than 33% homology with the 3' end in any naturally occurring tRNA.

4. A retroviral vector according to claim 1 in which up to 5 nucleotides 3' of the primer binding site have also been modified to a sequence that does not allow additional base pairing with a naturally occurring tRNA primer.

5. A host cell which has been transfected with a retroviral vector according to any of claims 1–4.

6. A packaging cell line for replication of a retroviral transfer vector according to any one of claims 1–4, where the cell line is a mammalian or avian cell line which has been transformed by the insertion of one or more vectors comprising a DNA sequence carrying the information for the production of viral proteins required in trans for retroviral replication, where the cell line has also been transformed by the insertion of a vector containing a DNA sequence comprising the structural gene sequence of a tRNA primer where said primer primes a primer binding site (PBS) that has been modified to a sequence that does not allow strong base pairing with the 3' end of any naturally occurring tRNA, and where the three 5' nucleotides of the PBS are UGG.

7. The packaging cell line of claim 6 where the tRNA structural gene encodes tRNA$^{pro}$, tRNA$^{gln1}$, tRNA$^{lys3}$, or tRNA$^{met(1)}$ and where the sequences involved in forming the secondary clover-leaf structure of the tRNA molecule by internal base pairing with the modified sequences are modified to be complementary therewith.

8. The packaging cell line of claim 7 where the tRNA is derived from tRNA$^{pro}$.

9. The packaging cell line of claim 8 where the DNA sequence comprising the structural gene sequence further includes a 5' leader sequence and a 3' sequence, encompassing the terminal signal TTTTT, corresponding to the flanking sequences of the murine tRNA$^{pro}$ gene.

* * * * *

UNITED STATES PATENT AND TRADEMARK OFFICE
CERTIFICATE OF CORRECTION

PATENT NO. : 6,037,172  
DATED : March 14, 2000  
INVENTOR(S) : F.S. Pedersen, A.H. Lund, J. Lovmand, P. Jorgensen, and M. Duch Page 1 of 1

It is certified that error appears in the above-identified patent and that said Letters Patent is hereby corrected as shown below:

Title page,
Item [56], References Cited, PUBLICATIONS:
"Pedersen, F.S. et al., "Control Points for Retroviral Vector Safety: A Look at t MLV Replication cycle", abstract of paper presented at Gostar. Germany, conferenc Sep. 18, 1994". should read:
-- Pedersen, F.S. et al., "Control Points for Retroviral Vector Safety: A Look at the MLV Replication cycle", abstract of paper presented at Gostar, Germany, Conference Sep. 18, 1994" --.

Column 8,
Line 13, "MRNA" in both instances should read : -- mRNA --.

Column 10,
Line 53, in column 4, "MMTMT1" should read: -- MMHMT1 --.

Signed and Sealed this

Fifth Day of February, 2002

Attest:

Attesting Officer

JAMES E. ROGAN  
*Director of the United States Patent and Trademark Office*